(12) United States Patent
Pearce et al.

(10) Patent No.: US 8,738,128 B2
(45) Date of Patent: May 27, 2014

(54) DEFIBRILLATOR/MONITOR SYSTEM HAVING A POD WITH LEADS CAPABLE OF WIRELESSLY COMMUNICATING

(75) Inventors: Christopher Pearce, Monroe, WA (US); Thomas J. McGrath, Everett, WA (US); Randy L. Merry, Woodinville, WA (US); John C. Daynes, Redmond, WA (US); Kenneth J. Peterson, Bellevue, WA (US); Peter Wung, Redmond, WA (US); Michael D. McMahon, Lake Forest Park, WA (US); D. Craig Edwards, Fall City, WA (US); Eric T. Hoierman, Bothell, WA (US); Rockland W. Nordness, Kirkland, WA (US); James S. Neumiller, Redmond, WA (US)

(73) Assignee: Physio-Control, Inc., Redmond, WA (US)

( * ) Notice: Subject to any disclaimer, the term of this patent is extended or adjusted under 35 U.S.C. 154(b) by 148 days.

(21) Appl. No.: 13/103,783

(22) Filed: May 9, 2011

(65) Prior Publication Data

US 2011/0208259 A1    Aug. 25, 2011

Related U.S. Application Data

(63) Continuation of application No. 10/583,209, filed as application No. PCT/US2004/042377 on Oct. 18, 2007, now Pat. No. 7,957,798.

(60) Provisional application No. 60/530,151, filed on Dec. 17, 2003.

(51) Int. Cl.
    *A61N 1/39*    (2006.01)

(52) U.S. Cl.
    USPC .................................... 607/5; 607/6; 607/8

(58) Field of Classification Search
    USPC ........................................... 607/3, 5–8
    See application file for complete search history.

(56) References Cited

U.S. PATENT DOCUMENTS

| | | | |
|---|---|---|---|
| 3,724,455 A * | 4/1973 | Unger | 600/515 |
| 3,865,101 A | 2/1975 | Saper | |
| 5,105,821 A * | 4/1992 | Reyes | 600/508 |
| 6,141,584 A * | 10/2000 | Rockwell et al. | 607/5 |
| 6,441,747 B1 | 8/2002 | Khair et al. | 340/870.16 |
| 6,978,181 B1 * | 12/2005 | Snell | 607/60 |
| 2004/0162586 A1 * | 8/2004 | Covey et al. | 607/5 |

OTHER PUBLICATIONS

International Preliminary Report on Patentability and Written Opinion, Jun. 20, 2006, 6 pages, International application No. PCT/US2004/042377, European Patent Office, Munich, Germany.

* cited by examiner

*Primary Examiner* — Joseph Dietrich
(74) *Attorney, Agent, or Firm* — Marger Johnson & McCollom, P.C.

(57) ABSTRACT

A modular external defibrillator system in embodiments of the teachings may include one or more of the following features: a base containing a defibrillator to deliver a defibrillation shock to a patient, (b) one or more pods each connectable to a patient via patient lead cables to collect at least one patient vital sign, the pods operable at a distance from the base, (c) a wireless communications link between the base and a selected one of the two or more pods to carry the at least one vital sign from the selected pod to the base, the selection being based on which pod is associated with the base.

30 Claims, 13 Drawing Sheets

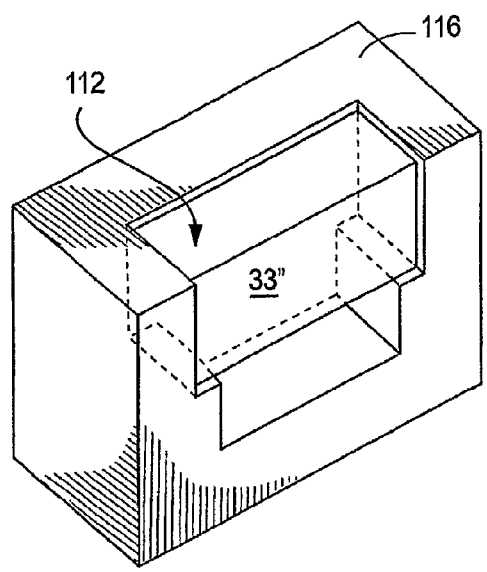
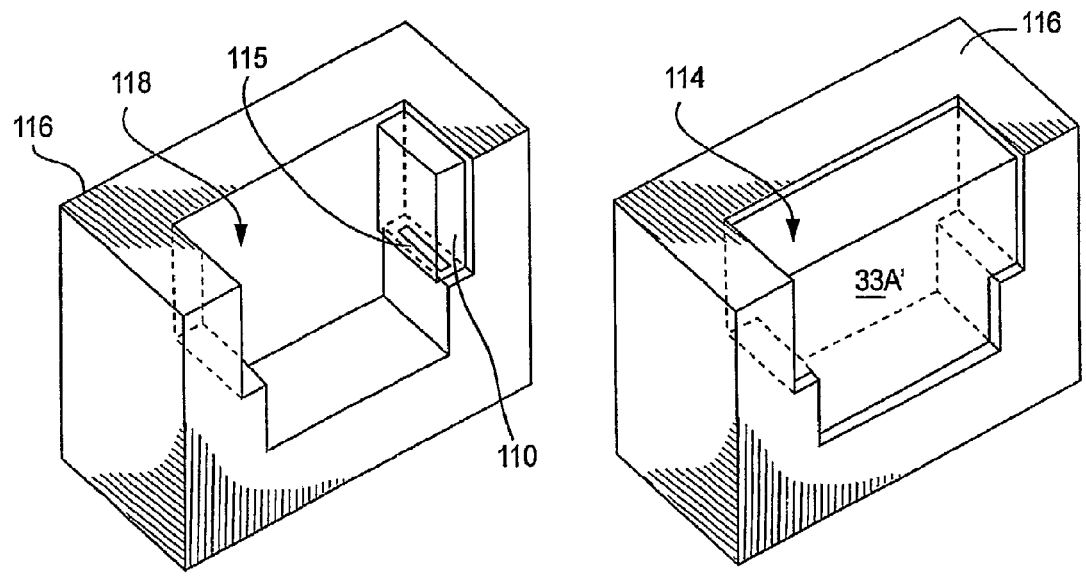
FIG. 6

DEFIBRILLATOR/MONITOR SYSTEM HAVING A POD WITH LEADS CAPABLE OF WIRELESSLY COMMUNICATING

This application is a continuation of U.S. patent application Ser. No. 10/583,209, filed Dec. 17, 2004, now U.S. Pat. No. 7,957,798, issued Jun. 7, 2011, which is a U.S. National Stage entry of PCT Application No. PCT/US2004/042377, filed Dec. 17, 2004, now published as WO2005/058417, which claimed priority to International PCT Application No. PCT/US2004/012421 filed on Apr. 22, 2004 and titled "Defibrillator/Monitor System Having a Pod with Leads Capable of Wirelessly Communicating," now published as WO2004/093979, and claimed the benefit of U.S. Provisional Application Ser. No. 60/530,151 titled "Defibrillator/Monitor System Having a Pod with Leads Capable of Wirelessly Communicating," all of which are hereby incorporated by reference in their entirety.

This disclosure is related to the following co-pending PCT applications entitled, "DEFIBRILLATOR PATIENT MONITORING POD," International Application No. PCT/US/2004/042792, filed Dec. 17, 2004, and "AN EXTERNAL DEFIBRILLATOR WITH POWER AND BATTERY SHARING CAPABILITIES WITH A POD," now published as WO2005/058413, International Application No. PCT/US2004/042376, filed Dec. 27, 2004, now published as WO2005/058416, which are both hereby incorporated by reference in their entirety and which are not admitted as prior art with respect to the present disclosure by their mention in this section.

TECHNICAL FIELD

The teachings relate to medical devices, and in particular, to defibrillation/monitor systems having a detachable pod with leads.

BACKGROUND

Each day thousands of Americans are victims of cardiac emergencies. Cardiac emergencies typically strike without warning, oftentimes striking people with no history of heart disease. The most common cardiac emergency is sudden cardiac arrest ("SCA"). It is estimated more than 1000 people per day are victims of SCA in the United States alone.

SCA occurs when the heart stops pumping blood. Usually SCA is due to abnormal electrical activity in the heart, resulting in an abnormal rhythm (arrhythmia). One such abnormal rhythm, ventricular fibrillation (VF), is caused by abnormal and very fast electrical activity in the heart. During VF the heart cannot pump blood effectively. Because blood may no longer be pumping effectively during VF, the chances of surviving decreases with time after the onset of the emergency. Brain damage can occur after the brain is deprived of oxygen for four to six minutes.

Applying an electric shock to the patient's heart through the use of a defibrillator treats VF. The shock clears the heart of the abnormal electrical activity (in a process called "defibrillation") by depolarizing a critical mass of myocardial cells to allow spontaneous organized myocardial depolarization to resume.

Cardiac arrest is a life-threatening medical condition that may be treated with external defibrillation. External defibrillation includes applying electrodes to the patient's chest and delivering an electric shock to the patient to depolarize the patient's heart and restore normal sinus rhythm. The chance a patient's heart can be successfully defibrillated increases significantly if a defibrillation pulse is applied quickly.

In a scenario where a patient on a gurney is being transported through narrow doorways and down stairwells to an ambulance, or the situation where a patient is in an ambulance moving on a road at high speed with patient cables and IV (intravenous) lines running between the patient and other equipment within the ambulance, if the monitoring/therapeutic device is large or the route to the ambulance is particularly difficult, the paramedic might elect to carry the device separately from the gurney to prevent the device falling off the gurney or onto the patient. However, the paramedic is now restricted in his or her ability to detach the device from the gurney due to the number and length of patient cables between the device and the patient. Similar restrictions occur once the patient is loaded into a patient transport vehicle or when the patient is transferred from the ambulance to the emergency department. The number of cables and their similarity in color or dissimilarity in length can all contribute to delays in treating or transferring the patient and can restrict the paramedic's mobility when treating the patient in a confined space. Additionally, delays may be created with cables having become tangled, or even cut, from their previous uses.

The prior art has tried to solve this problem by providing a wireless module that transmits data to a patient monitor, such as the MobiMed offered for Sale by Ortivus.

However, this device does not include a defibrillator and does not have the capability to provide any therapeutic functions such as pacing, defibrillation or synchronous cardioversion without attaching another monitor/defibrillator to the patient, which further increases the complexity and ambulance provider cost. Additionally, the Ortivus patient module does not offer replaceable batteries so functionality is severely limited if a reliable source of battery charging is not available, or if the transport time is excessively long. Additionally, the Ortivus device does not offer a display to allow visual monitoring of the waveforms or vital signs if the other module is out of range or obscured.

Another problem arises when hospital personnel want to charge the batteries of the defibrillator/monitor, but don't want to have to place the unit in a docking station in order to charge the batteries. There also arises the issue of patient confidentiality, such as recently raised by the Federal HIPAA (Health Insurance Portability and Accountability Act) regulations, when identical looking patient monitors are accidentally swapped by operators.

Another problem may occur in a situation where two or more sets of associated wireless devices are used in the same general area. This type of problem could occur in a number of different (medical or non-medical) applications. For example, medical device A is comprised of two parts, a patient data acquisition module (AA) and a display module (AD). The two parts communicate with each other via one of many wireless methods. Medical device B is comprised of two similar parts patient data acquisition module (BA) and display module (BD). In the event of a mass casualty incident, where medical personnel are attending to more than one patient, two or more patients may be laying close to each other. Suppose patient X is being attended to by the operator of device A, and a different operator who is using device B is attending to patient Y. Patient X's vital signs are being acquired by acquisition module AA and transmitted to display module AD. Patient Y's vital signs are being acquired by acquisition module BA and transmitted to display module BD. A problem could arise when, in the state of confusion typically existing in a mass casualty incident, the two display modules become switched. In this case, the operator of display module AD could be viewing the vital signs transmitted from Patient X while attending to Patient Y. This could result in inappropriate administration of drugs or other therapy with potentially serious consequences. The acquisition modules could still be associated to the appropriate display modules, and could still be functioning properly, but the operator could be viewing the wrong patient's vital signs.

Other problems with wireless communications include the fact wireless communications methods cannot be visually assessed by the operator prior to failure, such as a broken or damaged cable can. Wireless communications may not be permitted in critical areas, such as an aircraft environment, in military use, or elsewhere. Some wireless communications means have delays between sending a message and getting a response which are too long for therapeutic and other needs. There is a risk of the operator not being able to find a cable when, for instance, a critical therapy has to be administered where the wireless link cannot support it.

SUMMARY

A modular external defibrillator system in embodiments of the teachings may include one or more of the following features: (a) a base containing a defibrillator to deliver a defibrillation shock to a patient, (b) one or more pods each connectable to a patient via patient lead cables to collect at least one patient vital sign, the pods operable at a distance from the base, and (c) a wireless communications link between the base and a selected one of the one or more pods to carry the at least one vital sign from the selected pod to the base, the selection being based on which pod is associated with the base.

A modular external defibrillator system in embodiments of the teachings may include one or more of the following features: (a) a base containing a defibrillator module to deliver a defibrillation shock to a patient, (b) two or more pods each having a patient parameter module and connectable to a patient via patient lead cables to collect at least one patient vital sign, the pods operable at a distance from the base, and (c) wireless communications links between the base and the two or more pods to carry the at least one vital sign from each pod to the base, the base having a monitor portion to display the at least one vital sign received from a selected one of the two or more pods.

A method of associating components in a modular external defibrillator system in embodiments of the teachings may include one or more of the following steps: (a) providing a base containing a defibrillator to deliver a defibrillation shock to a patient, (b) selecting a patient parameter pod to associate with the base, the selected pod being connectable to a patient via patient lead cables to collect patient data, the selected pod being operable separate from the base, (c) establishing a communications link between the base and the selected pod to carry the patient data from the pod to the base, and (d) testing the communications link to determine if association is successful.

BRIEF DESCRIPTION OF DRAWINGS

FIG. 6 is a diagram of a patient module pod and a defibrillator/monitor based interaction in an embodiment of the present teachings;

DETAILED DESCRIPTION

Figure 1:
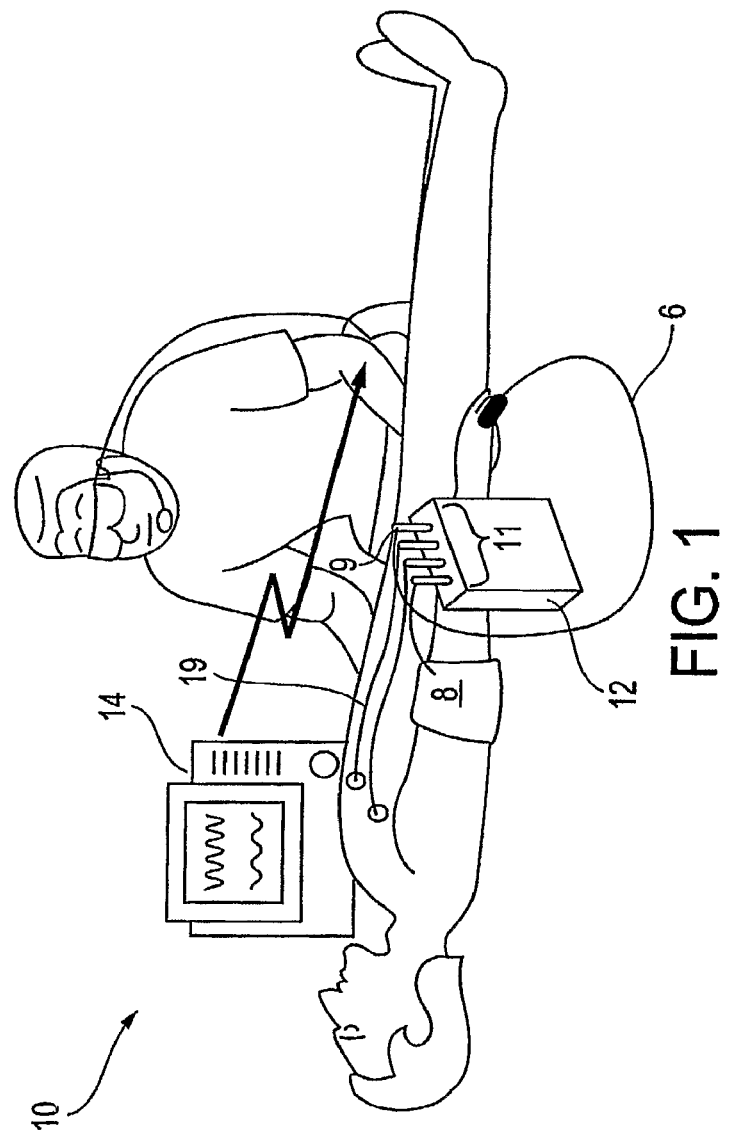
FIG. 1 is a pictorial representation of an external defibrillator having a patient module pod with a defibrillator/monitor base in an embodiment of the present teachings.

The following discussion is presented to enable a person skilled in the art to make and use the present teachings. Various modifications to the illustrated embodiments will be readily apparent to those skilled in the art, and the generic principles herein may be applied to other embodiments and applications without departing from the present teachings. Thus, the present teachings are not intended to be limited to the embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives that fall within the scope of the present teachings.

With reference to FIG. 1, a pictorial representation of an external defibrillator having a patient module with a defibrillator/monitor in an embodiment of the present teachings is shown. External defibrillator 10 is comprised of two components patient module (pod) 12 and defibrillator/monitor (base) 14, which communicate patient data (e.g., vital signs) and share common replaceable battery technology. Pod 12 generally rests within base 14, generally in the back of base 14. The operator, during an emergency, has the option of carrying base 14 with pod 12 attached or simply carrying pod 12 to the emergency site. Since pod 12 is smaller and lighter than base 14, generally it will be easier for the operator to simply carry pod 12. By carrying pod 12, the operator is free to carry more ALS equipment and not be slowed by the heavier and more awkward base 14.

Pod 12 connects to a patient via several leads in order to measure the patient's vital signs. Pod 12 communicates the patient's vital signs either wirelessly or via an electrical connection to defibrillator monitor 14. The patient data or vital signs collected may include 3, 4, and 5 lead ECG readings, 12 lead ECG readings, non-invasive blood pressure (NIBP), pulse oximeter data, capnography data, invasive blood pressure, body temperature, $CO_2$ levels, and additional patient monitoring functions. Additionally, pod 12 may include a small display 82 (FIG. 4) replicating some or all of the information such as waveforms, numerical data, and vital signs being transmitted to base 14. The patient data or vital signs may be collected with a multitude of leads 11 such as an ECG lead 19, a non-invasive blood pressure lead 8, and pulse oximeter lead 6, extending from patient lead cable port 9 that may include many inputs if multiple lead cables are used.

Base 14 includes a therapy module 56 (FIG. 3) and therapy cables. Therapy module 56 has the capability to provide therapeutic functions such as pacing, defibrillation, or synchronous cardioversion without attaching another monitor/defibrillator to the patient. The therapy cables typically include patient paddles or electrodes that attach between the patient and base 14 in order to deliver the therapy to the patient. Since pod 12 connects to the patient and transmits vital signs to base 14, then base 14 need not also have patient monitoring cables. Accordingly, paramedic mobility and ease of use are greatly increased. Therapy module 56 in base 14 may be configurable in either an ALS mode or an AED mode. The ALS mode includes a multi-parameter monitoring capability and all of the defibrillator therapy delivery capability. Additionally base unit 14 may be just an AED.

Figure 2:
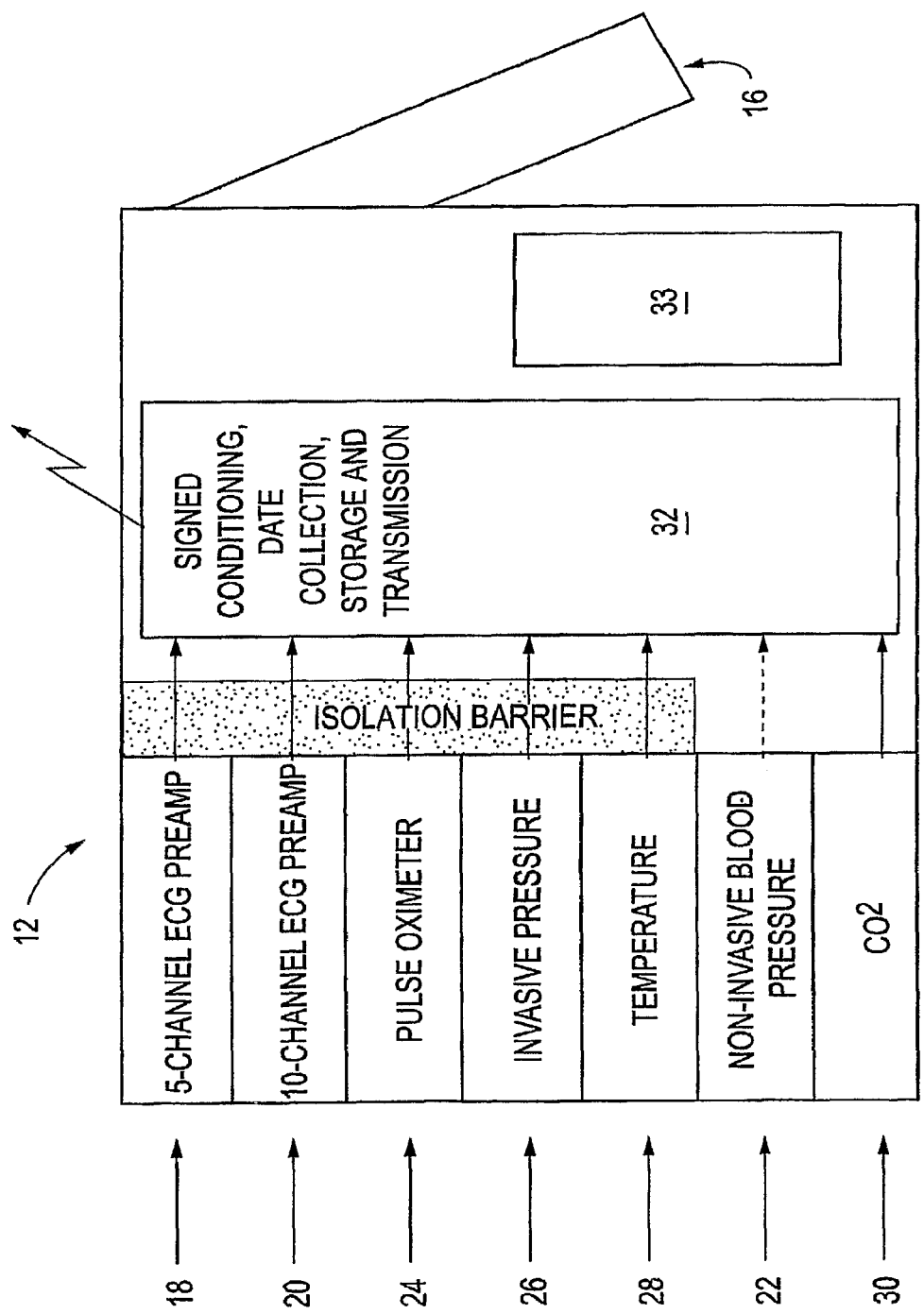
FIG. 2 is an upper level pictorial representation of a patient module pod in an embodiment of the present teachings.

With reference to FIG. 2, an upper level pictorial representation of a patient module in an embodiment of the present teachings is shown. Generally, pod 12 uses replaceable or rechargeable batteries 16 for power and comprises any combination of the following features: 3, 4, and 5 lead ECG inputs 18, 12 lead ECG inputs 20, non-invasive blood pressure (NIBP) input 22, pulse oximeter input 24, capnography input (not shown), invasive blood pressure input 26, temperature input 28, $CO_2$ input 30, additional patient monitoring functions, transceiver 32 to transmit any or all real time patient data to base 14. Transceiver 32 can be a wireless BlueTooth module commercially available from TDK, however, transceiver 32 can be any transceiver such as WiFi (802.11), Wireless WAN(CDMA, GSM, GPRS, UTMS, etc.), or a wired Fire-Wire (IEEE 1394) without departing from the spirit of the present teachings. Additionally, pod 12 may include a small display 82 (FIG. 4) replicating some or all of the information such as waveforms, numerical data, and vital signs being transmitted to base 14. Additionally, pod 12 includes some means by which it can be attached and secured to base 14 for the purpose of carrying base 14 to an emergency scene as is discussed in PCT Application Serial No. US04/12421. Additionally, pod 12 may have a feature allowing it to be easily secured to a gurney or hospital bed.

Figure 3:
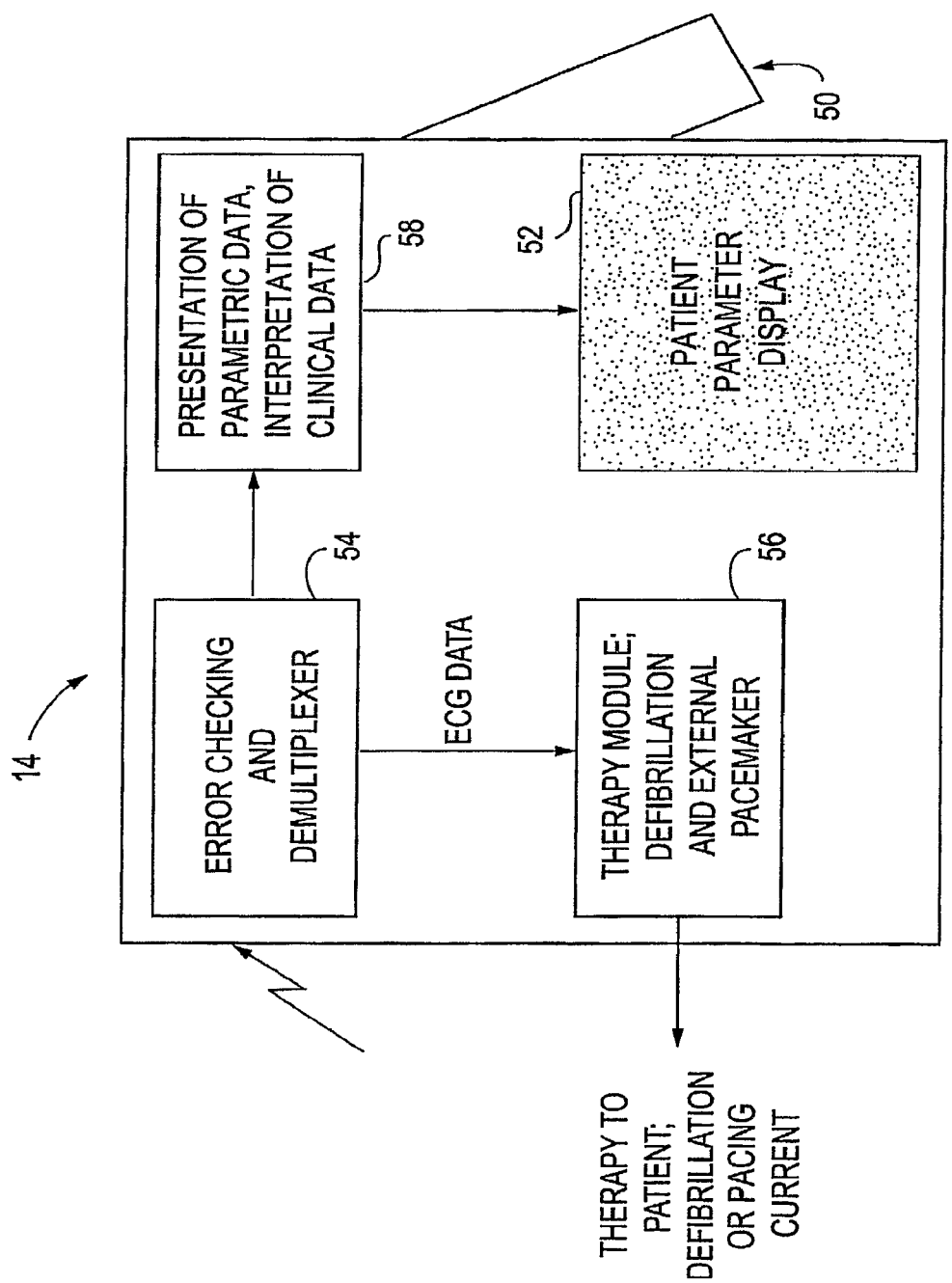
FIG. 3 is an upper level pictorial representation of a defibrillator/monitor base in an embodiment of the present teachings.

With reference to FIG. 3, an upper level pictorial representation of a defibrillator/monitor in an embodiment of the present teachings is shown. Base 14 uses a replaceable or rechargeable battery 50 for power. Batteries 16 and 50 are generally similar in battery chemistry, electrical, and mechanical features to permit the interchangeability between batteries 16 and 50. Batteries 16 and 50 can be a LiIon battery providing 16 volts and 3.8 amps, however, most any type of battery can be used without departing from the spirit of the invention. Additionally, base 14 comprises a display 52 sufficient to show current and historical patient data, a transceiver (similar to transceiver 32 [not shown]) to send acquired patient data onto a receiving station or third party data receiver, a module 56 to synchronize shocks and pacing pulses to the patient's intrinsic rhythm from data acquired by a pod 12, an error checking and de-multiplexing module 54 receiving and processing data received from pod 12, and a data interpretation module 58 which analyzes data acquired by pod 12 and makes certain interpretive statements on the patient's cardiac or respiratory condition, displays vital sign trends, and provides additional functions found in ALS monitoring products.

Figure 4:
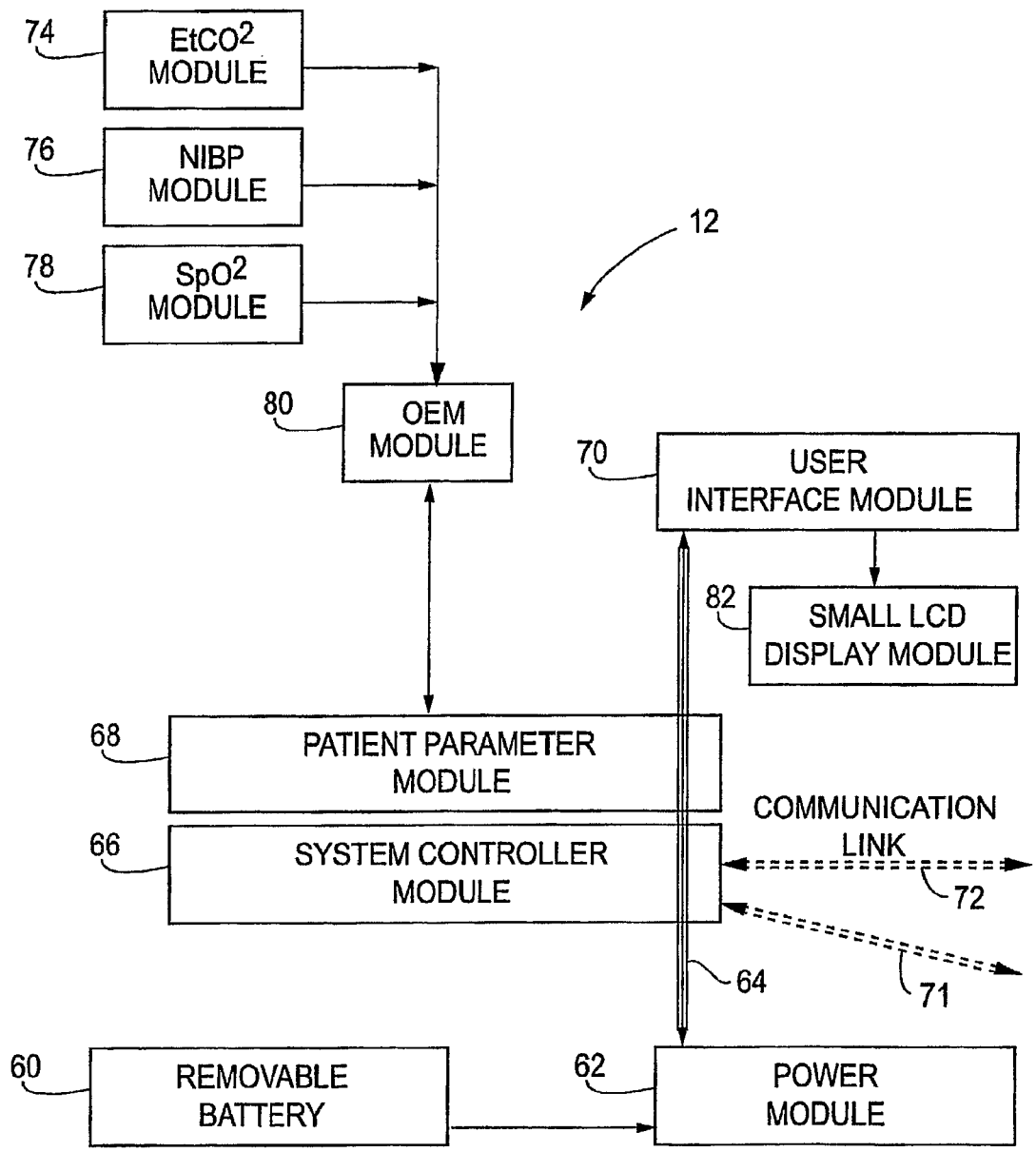
FIG. 4 is a schematic view of a patient module pod in an embodiment of the present teachings.

With reference to FIG. 4, system controller module 66 controls interaction of all the pod's modules through data bus 64 and interaction with base 14 through a wired connection, such as tethered cable 46 or wireless (e.g., IrDA, RF, etc.) communication link 72 which would be transmitted by transceiver 32 incorporated into system controller 66 as part of an interconnect module. System controller module 66 has the ability to encrypt data communicated over the wireless links to meet HIPAA requirements for the protection of patient data. There can be a single encryption key for all bases and pods. However, it is contemplated there could be a user defined encryption key that can be set at the base by an operator. Patient parameter module 68 monitors functions such as invasive blood pressure, patient's temperature, and inputs from the pod leads. Module 68 further collects inputs from $EtCO_2$ module 74, NIBP module 76, and $SpO_2$ module 78 through OEM module 80. Patient parameter module 68 takes all of these inputs and processes them for display and can route only a limited number of inputs to small LCD display module 82 through operator interface module 70. Patient Parameter Module 68 also has the ability to perform interpretation of clinical data and can make certain interpretive statements about the patient's condition (e.g., cardiac or respiratory health).

Power module 62 provides on/off control to the pod, utilizing the removable battery 60 as the power source. Additional power management options are disclosed in PCT application titled, "AN EXTERNAL DEFIBRILLATOR WITH POWER AND BATTERY SHARING CAPABILITIES WITH A POD," International Application No. PCT/US2004/042376, filed Dec. 17, 2004, incorporated by reference above.

Operator Interface module 70 allows the operator to primarily interact with pod 12; however, it is contemplated that operator could use the module 70 to interact with base 14 as well.

Figure 4A:
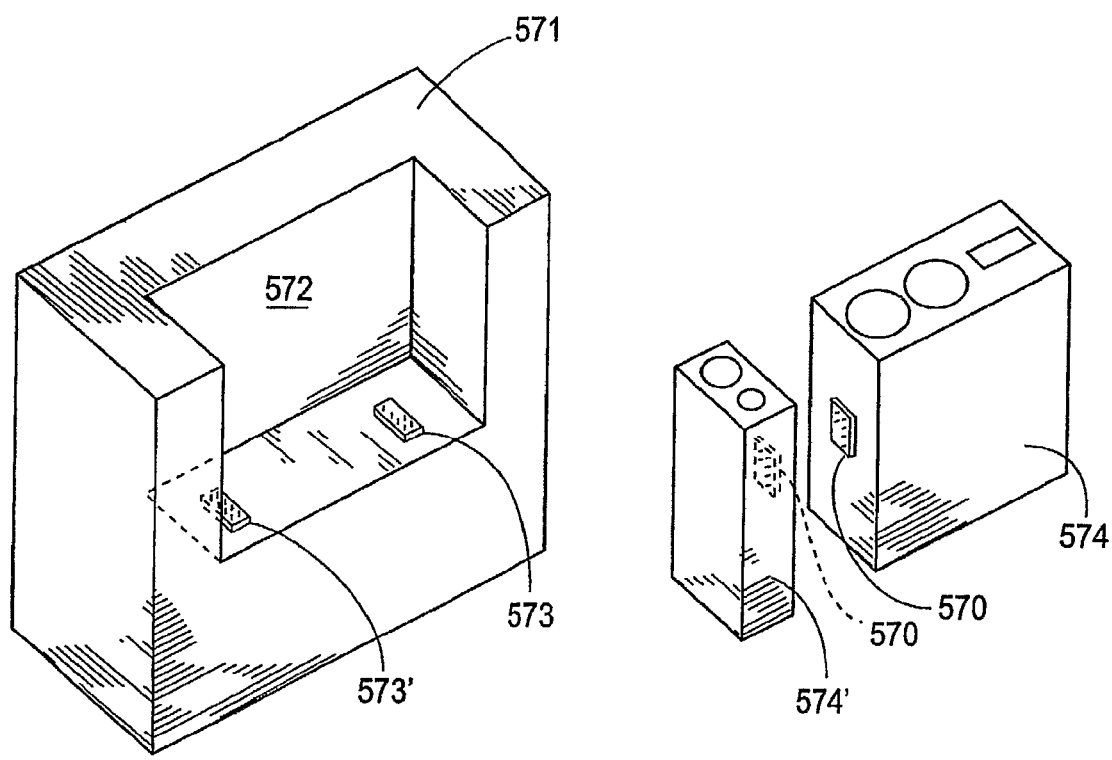
FIG. 4A is a pictorial representation of a multiple patient module pod storage and attachment assembly in an embodiment of the present teachings.

With reference to FIG. 4A, a pictorial representation of a multiple patient module storage and attachment assembly in an embodiment of the present invention is shown. Pods can come in different sizes generally representing the capability of the pod. For example, smaller pod 574' would provide only the basic features for an external defibrillator, while medium pod 574 would provide several additional features. In the present embodiment, pods 574 and 574' can be docked together in mounting recess or slot 572 contemporaneously. In one embodiment, pod 574 could be latched within mounting slot 572 communicating with base 571 through connector 573. Similarly, pod 574' can be placed within mounting slot 572 contemporaneously with pod 574 and latched in a communicating relationship with base 571 through connector 573'. In another embodiment, pods 574 and 574' could be placed within mounting slot 572 without the need for two base-to-pod connectors 573. Pod 574 and 574' latch together and communicate through connectors 570. Then both pods 574 and 574' are placed within mounting slot 572 and latched in a communicating relationship with base 571 through connector 573. This embodiment not only limits the amount of connectors needed on base 571, but also allows the user to choose the amount of functions the pod can perform. For example, if the user simply needed to perform an ECG, then the user could choose to carry small pod 574'. However, if the emergency situation required additional functions such as monitoring blood pressure in a non-invasive method or a pulse oximeter, then the user would choose to carry medium pod 574'. In addition, if the emergency situation required all of the available pod functions, then pod 574' could be latched together with pod 574 to provide a large pod having all necessary functions. It is also further contemplated connectors 573, 573', and 570 could be most any type of connector such as a USB port, an AC power connector, an RS-232 connector or any other type of connector known to those skilled in the art without departing from the spirit of the invention.

Figure 9:
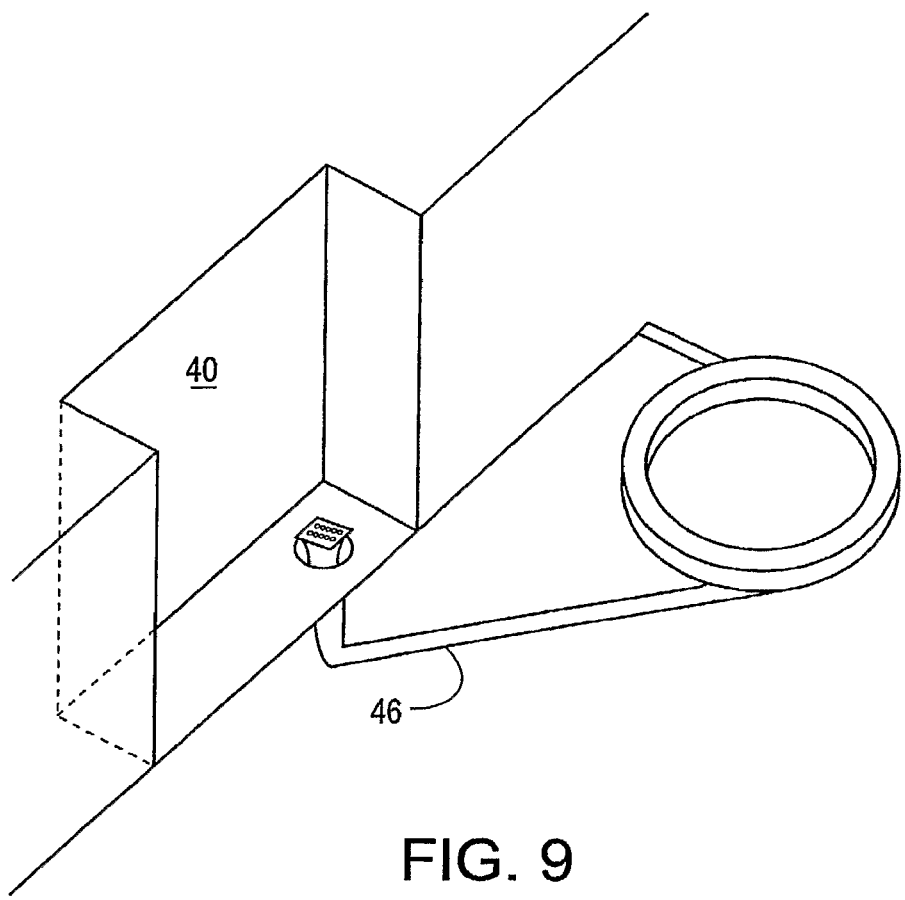
FIG. 9 is a pictorial representation of a connector in an embodiment of the present teachings.
Figure 10:
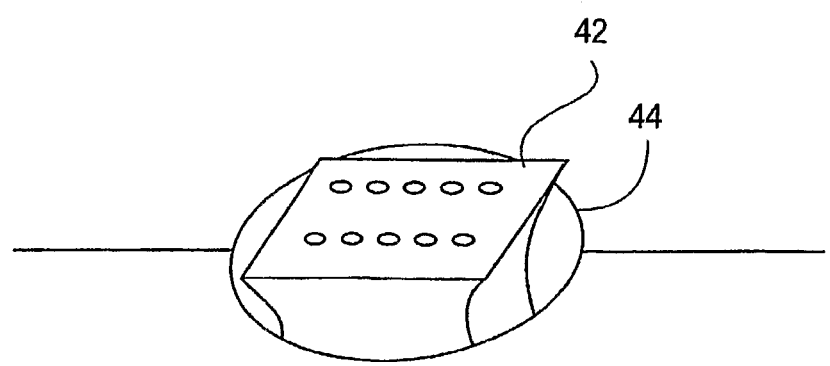
FIG. 10 is a pictorial representation of a mating assembly having a tethered connector in an embodiment of the present teachings.

With reference to FIGS. 9 and 10, a pictorial representation of a mating assembly having a tethered connector in an embodiment of the present teachings is shown. In this embodiment, a pod similar to 12 rests within slot 40 and connects to base-to-pod connector 42, which allows base 14 and a pod to communicate with each other. Base-to-pod connector 42 rests freely within connector cavity 44, which allows connector cable 46 to retractably exit and enter base 14 as shown in FIGS. 9 and 10. Tethered cable 46 allows a pod to mate with and rest within base 14 or mate with base 14 when not docked within slot 40. It is sometimes helpful that base 14 communicate with a pod through tethered cable 46 since communications through a direct connection is generally faster. This is the case in the present embodiment as base 14 is equipped with a high speed bus, such as a USB bus, which provides quick communication of information between a pod and base 14. Base 14 is also able to automatically detect when tethered cable 46 is plugged in so direct communications can be established immediately. A direct communication between a pod and base 14 can be established. This automatic establishment of direct communication between a pod and base 14 includes when a pod is docked within base 14 and a connection is made between a pod and base 14 through connector 42.

Generally base 14 and a pod communicate wirelessly to assist in preventing the tangling of cables, which can occur between a patient and base 14, particularly when transporting patients. Tethered cable 46 (or a direct connect via ports in the base and pod) provides a system for use when the wireless link between pod 12 and base 14 fails for whatever reason or when precise signal synchronization demands a wired connection. Tethered cable 46 also provides the added advantage in that the user cannot lose cable 46 because it is tethered to base 14. Wireless links can impose a delay in communication between a pod and base 14 longer than may be experienced with a cable. When communications between base 14 and a pod require a faster response time (such as application of synchronous cardioversion or pacing where information from a pod must be transmitted to base 14), the user is advised of the need to plug cable 46 into the pod. The user is provided a user interface message to inform them of the need to attach cable 46 or to dock pod on base and establish a direct wired connection.

With reference again to FIG. 4, system controller module 66 controls interaction of all the pod's modules through data bus 64 and interaction with base 14 through a wired connection, such as tethered cable 46 or wireless (e.g., IrDA, RF, etc.) communication link 72 which would be transmitted by transceiver 32. System control module 66 may also include an interconnect module to assist with wire and wireless communications over link 72. Patient parameter module 68 monitors functions such as invasive blood pressure, patient's temperature, and inputs from the pod leads. Module 68 further collects inputs from $EtCO_2$ module 74, NIBP module 76, and $SpO_2$ module 78 through OEM module 80. Patient parameter module 68 takes all of these inputs and processes them for display and can route only a limited number of inputs to small LCD display module 82 through operator interface module 70. Operator Interface module 70 allows the operator to primarily interact with pod 12; however, it is contemplated that operator could use the module 70 to interact with base 14 as well.

Figure 5:
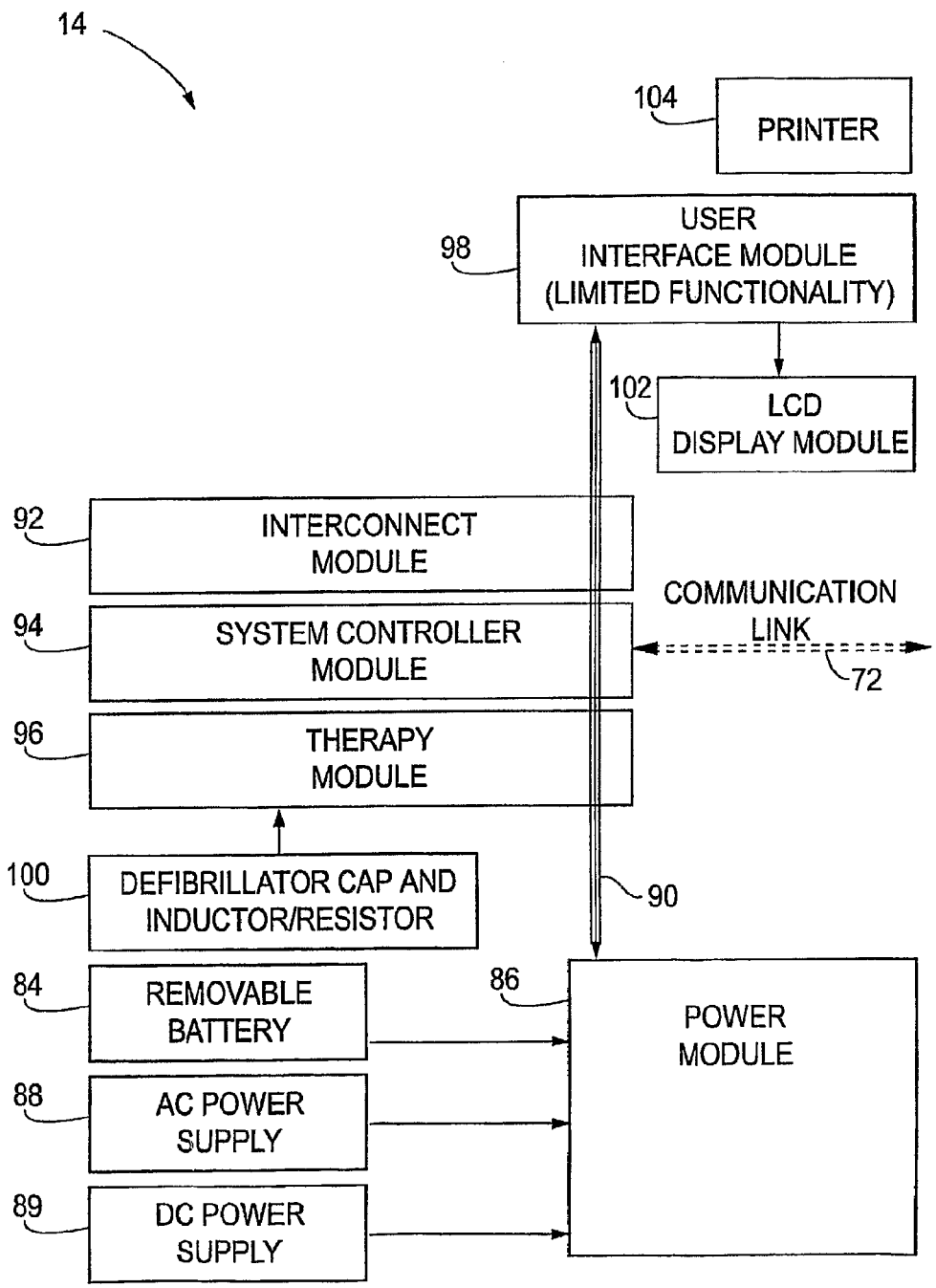
FIG. 5 is a schematic view of a defibrillator/monitor base in an embodiment of the present teachings.

With reference to FIG. 5, a schematic view of a defibrillator/monitor in an embodiment of the present teachings is shown. Base 14 is powered by a removable/rechargeable battery 84, which provides power to power module 86. Alternatively, base 14 could be powered by AC power supply 88 or DC power supply 93. Power module 86 processes the incoming power into appropriate powered levels for each of the internal components. Power module 86 also routes the base's power supply through main power and data bus 90 to interconnect module 92, system controller module 94, therapy module 96, and operator interface module 98. Interconnect module 92 is utilized to detect how pod 12 is connected to base 14 (wirelessly, docked, or tethered cable). Although interconnect module 92 is utilized to detect how pod 12 is connected to base 14, interconnect module 92 can route the power provided from power module 86 to the pod 12 as discussed in PCT application titled, "AN EXTERNAL DEFIBRILLATOR WITH POWER AND BATTERY SHARING CAPABILITIES WITH A POD," International Application No. PCT/US2004/042376, filed Dec. 17, 2004, which is incorporated by reference above. Additionally, interconnect module 92, in conjunction with system controller 94, stores all of the information about the associations that have been established between the base 12 and pod 14. Similar to system controller module 66 (in FIG. 4), system controller module 94 controls all interaction of all of the base's modules through data bus 90 and interaction with pod 12 through wired or wireless connection communication link 72 or through data bus 90 if pod 12 is connected to the base 14. System controller module 94 and interconnect module 92 have the ability to encrypt data communicated over the wireless links to meet HIPAA requirements for the protection of patient data. Therapy module 96 synchronizes shocks and pacing pulses to the patient's intrinsic rhythm from data acquired from pod 12. Module 96 administers shocks from voltages via the defibrillation cap 100 and, in turn, administers packing pulses to a patient. Operator interface module 98 allows the operator to primarily interact with base 14; however, it is contemplated that the operator could use the module 98 to interact with pod 12 as well. For example, patient demographic data (e.g., age, sex, height, weight) could be entered at the base 14, and communicated to the pod 12 for use in interpretive algorithms performed in system controller 66 within pod 12. LCD module 102 allows the operator to view a patient's monitored parameters. Finally, the operator has the option to print out patient information on a printer 104 (e.g., a 100 mm strip chart printer).

With reference to FIG. 6, a diagram of a patient module pod and a defibrillator/monitor base interaction in an embodiment of the present teachings is shown.

In the present embodiment, the pods are all scalable. For example, a small pod 110 may provide basic functionality such as ECG acquisition and capability to administer a corrective therapy and the ability to measure $SpO_2$. A medium sized pod 112 may provide all the basics of small pod 110 and provide additional functionality such as measuring $CO_2$ and NIBP. And finally, a large pod 114 may provide the operator all the functionality of pod 12. The present embodiment allows for the automatic "association" or "pairing" of base 116 with any of pods 110, 112, and/or 114. Therefore, if small 110, medium 112, or large pod 114 were placed within slot 118 in base 116, base 116 could automatically detect what size of pod it was being associated with and then match the pod with base 116. In prior solutions, scalability was limited to the base unit. The present embodiment allows for the scalability to be outside of base 116 and instead with pods 110, 112, and 114. Automatic association provides the ability for base 116 to identify the capability of pods 110, 112, and 114 without any operator input.

Figure 7:
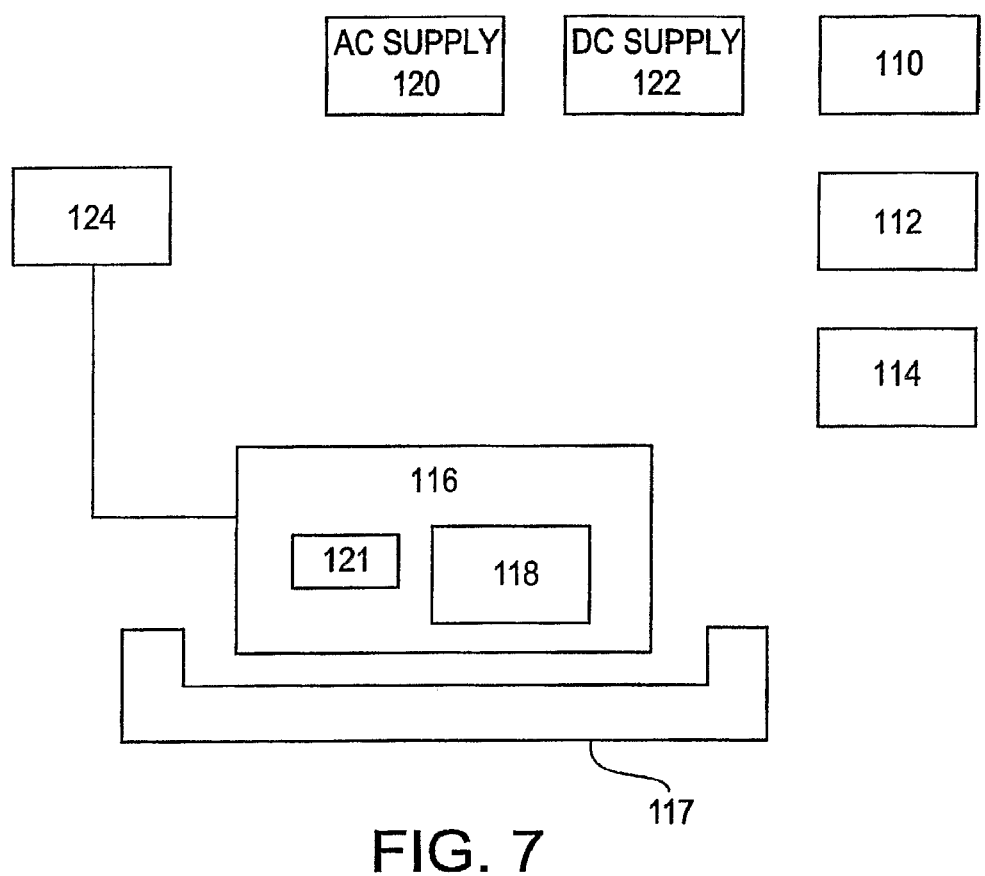
FIG. 7 is a block diagram of different size a patient module pods a defibrillator/monitor base, a base docking station, AC or DC power supplies, and a personal computer interaction in an embodiment of the present teachings.

With reference to FIG. 7, a block diagram of a patient module pod and a defibrillator/monitor base interaction in an embodiment of the present teachings is shown. The concept of an automatic association can be extended to AC power supply 120 and DC power supply 122, where base 116 could communicate battery type and status to the power supply providing power to the base 116 to control the transfer of power for device operation and battery charging. If base 116 is able to automatically pair with a power supply and adapt to the power supply's behavior, there is a reduced need for a docking station 117 to provide power or to recharge batteries 16 and 50. Such behavior adaptation could include determining automatically how fast the battery could charge and just exactly what type of circuitry could be used for charging depending on whether AC power source 120 or DC power source 122 was being used. It is contemplated base 116 could, similar to pods 110, 112, and 114, have a similar scalability in that smaller base stations may have a lower capacity. Furthermore, it is contemplated base 116 could be connected to a personal computer 124 where PC configuration files contain the hardware and software compatibility between the base and the pod. These files could be stored on PC software and when needed could be downloaded to base 116. Therefore, this could limit the amount of information needed on base 116 with respect to all the possible combinations regarding compatibility between the base stations and the pods. It is contemplated this automatic association of power supplies or rechargeable batteries could be extended to pods 110, 112, and 114, which could make pods 110, 112, and 114 stand alone devices.

Figure 8:
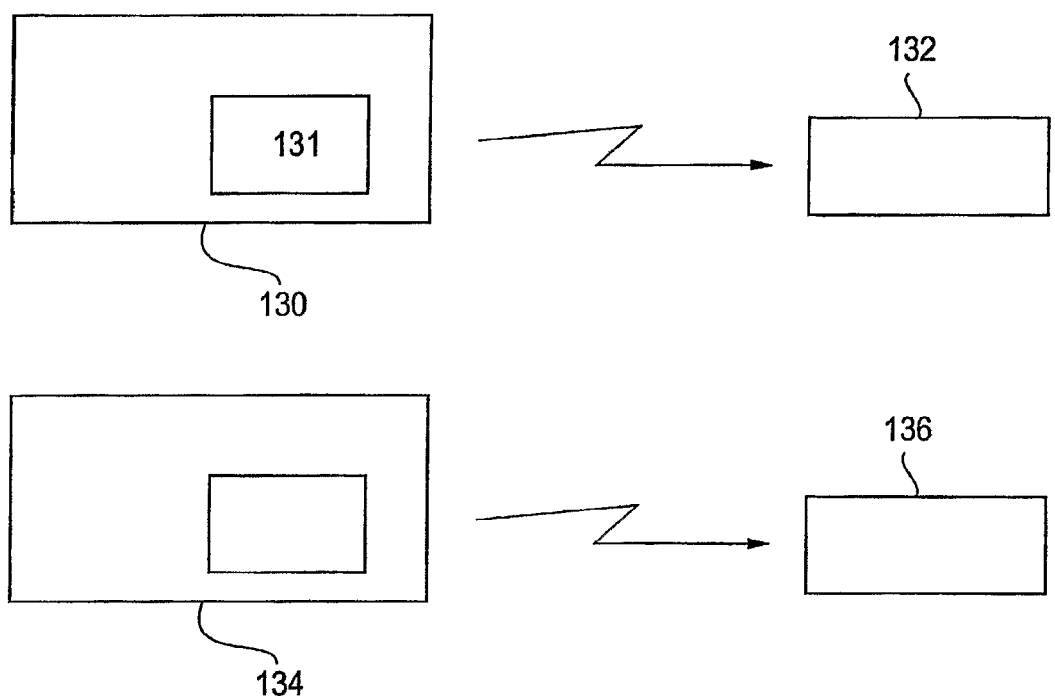
FIG. 8 is a block level diagram of an association system for a patient module pod and a defibrillator/monitor base in an embodiment of the present teachings.

With reference to FIG. 8, a block level diagram of an association system for a patient module pod and a defibrillator/monitor base in an embodiment of the present teachings is shown. The present embodiment facilitates the association of pods 132 and 136 with bases 130 and 134 respectively and pre-establishing the authorized combination of the devices. It is helpful the operator have minimal or no input with the association of the pods with the bases.

In some embodiments, the association is made by use of a direct connection either via docking and connection with connector 115 or connector 115 could be tethered to the base for removal from the base and connection to a remote pod as discussed above. Therefore, the first time the units are powered up, the devices automatically begin the association process. This can be referred to as dynamic association. Each pod 132, 136 stores a preset unique identifier. The identifier may be stored in the system control module 66 (FIG. 4) of pod 132. Once pod 132 was placed within port 131, base 130 could interrogate pod 132 requesting identification to determine its unique identifier stored within pod 132. Pod 132 would electrically transfer its unique identifier to base 130. Base 130 can store the unique identifier for this "selected" pod 132 in the systems control module 94 (FIG. 5) of base 130. Accordingly, if the pod 132 is then separated from base 130, wireless communication may occur between these associated or paired devices over respective communication links 72 (FIGS. 4 and 5).

As noted above, the wireless communication over link 72 may be via a wireless BlueTooth module, or using other communication protocols, such as WiFi (802.11), Wireless WAN (CDMA, GSM, GPRS, UTMS, etc.). For instance, assuming the communication occurs via WiFi, pod 132 will begin to transmit a beacon on a preselected channel once it is unplugged from base 130. Base 130 will then search for its associated pod. Under common 802.11 protocol, the base may start by searching a default frequency channel in the channels commonly available, then base 130 would scan over a sequence of channels and look for valid 802.11 devices (e.g., pods) transmitting a beacon signal.

Once the base 130 finds a valid 802.11 device (e.g., a pod transmitting a beacon signal), it will check whether this is the associated pod by querying the pod's identifier. If the base has found its associated pod, the devices may begin wireless communication as is known under this protocol. If the channel used for the initial communication is crowded (e.g., noisy or other devices broadcasting on the same channel), provisions are in place in wireless technologies, such as 802.11 and bluetooth, to automatically conduct channel hopping to find a clearer channel.

Association can also accomplished via wireless means. For instance, with pod 132 and base 130 separated, an operator could manually initiate their association. In this scenario, an operator would input a command or press a key on user interface module 98 (FIG. 5) of base 130 and on user interface module 70 (FIG. 4) on pod 132 that initiate the association. Both base 130 and pod 132 would then transmit a beacon signal on preselected frequencies that includes a known tag or flag that convey to each other that these are the base and pod to be associated. Base 130 could scan for the pod transmitting this tag following a process described above under the standard communication protocols. Once the base found a pod transmitting a beacon signal, the base would "listen" to the beacon signal to see whether the pod is transmitting the known flag indicating that it is the pod to be associated. If so, then the base 130 would query this pod for its unique identifier. Instead of transmitting this identifier electrically, as a docked pod would, this remote pod transmits its identifier wirelessly to base 130. The pod and base would then be associated and could begin communication as described above.

In addition to manual wireless association, association can also be automatically accomplished with the 132 and base 130 through a wireless communication of pre-established authentication and authorization information stored within the system controller module 94 and interconnect module 92 within the base 130.

Dynamic association is especially helpful if a pod were to fail and the operator desired to put another pod in its place. For example, if pod 132 were to fail, then pod 136 could be docked in slot 131 and base 130 could dynamically pair new pod 136 with base 130. To verify the association was successful, the operator can press a button on base 130 or pod 136, which could initiate an audible confirmation and/or a visual LED on the respective pod or base.

Figure 11:
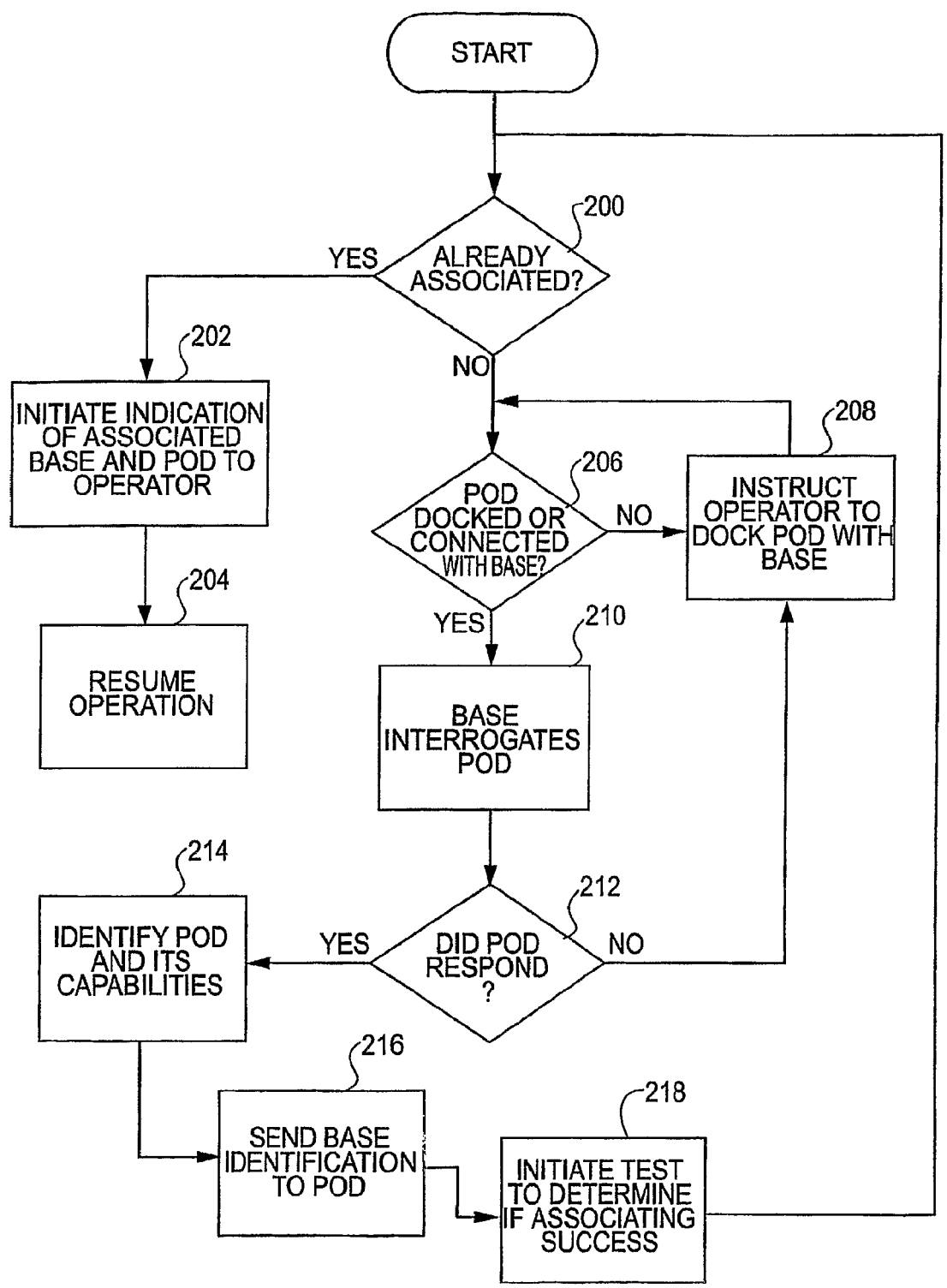
FIG. 11 is a flow diagram of association between a device and a base in an embodiment of the present teachings.

With reference to FIG. 11, a flow diagram of association between a pod and a base in an embodiment of the present teachings is shown. At state 200, initial communication is made between a pod and base 14. This can occur during docking of the pod with base 14, connecting cable 46 with the pod, or wireless communications between base 14 and the pod. Base 14 interrogates the pod requesting pod identification. Upon receiving pod identification from the pod, the base then determines whether this is the last pod to which it was associated. If the pod is the same pod to which base 14 was associated and indication is given to the operator that the pod is currently associated with base 14 at state 202. The operator can associate a name with each pod unique identifier to aid in human understanding. The operator indication can be an audible alarm, a visual indicator, a message on display 102, or a digitized voice without departing from the present teachings. Once association is determined base 14 and the pod resume operation together at state 204.

If base 14 determines it is not currently associated with the pod or that it has not been associated with any pod, base 14 determines whether the pod is either docked with base 14 or connected via cable 46 with the pod at state 206 by interrogating the pod 12 over the wired portion 46 of communication link 72. If the pod is not docked or connected with base 14, base 14 instructs the user to either dock the pod with base 14 or connect the pod via cable 46 at state 208. The operator instruction remains until it is determined at state 206 that the pod has been docked or connected. Once this occurs, base 14 interrogates the pod over the wired portion 46 of the communication link 72, requesting the pod's unique identifier at state 210. Base 14 then waits for a response from the pod at state 212. If the pod does not respond or a predetermined period of time passes, the operator is once again instructed to dock the pod or connect it via cable 46 at state 208. Once base 14 identifies the pod, the pod identification information is compared against information stored in the system controller 94 of the base 14 indicating if base 14 is associated with pod 12. Once the association is identified at state 214 all the capabilities of the pod 12 are communicated from pod 12 to base 14 so base 14 can interact with the pod utilizing all the pod's capabilities. It is fully contemplated pod identification could be accomplished in other fashions such as having a look-up table stored in base 14, downloading the information from a personal computer, or communicating with a network without departing from the spirit of the present teachings. At state 216, base 14 transfers its identification information to the pod so the pod can identify and store in system controller 66 memory which base 14 it is currently associated with. Base 14 then initiates a test with the pod to confirm that base 14 and the pod 12 are properly associated at state 218.

Figure 12:
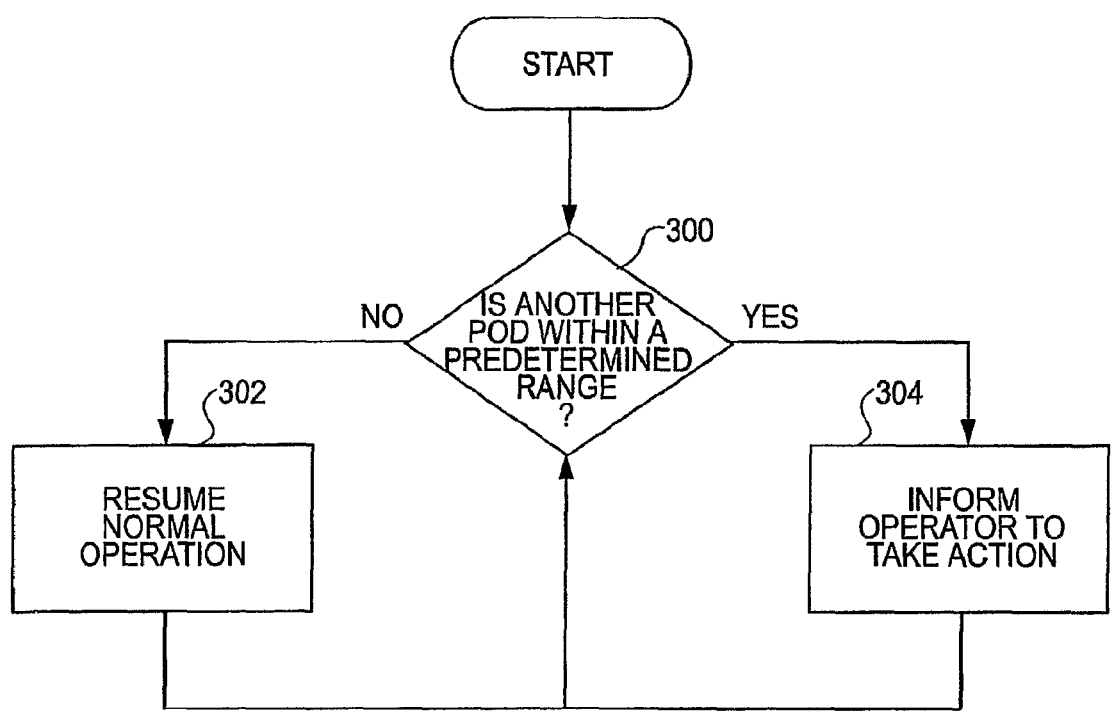
FIG. 12 is a flow diagram of patient monitoring pod identification function in an embodiment of the present teachings.

Proper pod and base association is a helpful aspect in accordance with some embodiments of the system. With further reference to FIG. 12, an embodiment allows for immediate identification of which patient pod should be displayed when a plurality of pods and bases are in close proximity. It can be contemplated that confusion can occur at a base when multiple pods are available for communication. Each pod responds to the base with a unique identifier over the communication link 72. The communication link 72 uses the unique identifier to ensure communication with the correct pod. The unique identifier is preset in a wireless communication module or portion of the pod's system control module 66. The operator can associate a name with each pod unique identifier that will be displayed on the base display 102 to inform the operator of the association with such pod. The unique identifier facilitates the establishment of the specific communication links to avoid crosstalk.

In certain embodiments, base 130 could sense the proximity of another pod 132 within its range and alert the operator of the other pod's presence at state 300. Each pod routinely transmitting an identifying wireless signal could accomplish the proximity sensing. However, other methods of proximity sensing could be used such as each pod routinely transmitting an audible sound without departing from the spirit of the present teachings. If no other pod is sensed within the base's proximity, then base 130 resumes normal operation at state 302. If another pod is detected within the base's proximity, then the operator may then be directed to interact with the base or pod, for example, by manually pressing a locator button 121 (FIG. 7) thereon at state 304. This action could cause the pod or base to respond in some way (e.g. visual or audible alert) to let the operator know which is the proper mate to the base or pod. The operator could also attach serial cable 46 to pod 132 or momentarily plug patient pod 132 into slot 131 of base 130. Whether by a cable or by docking pod 132, pod 132 and base 130 identify each other, and communicate only with each other until another such mating of a different pod with base 130 occurs. In this way, an operator could determine whether or not the pod association had accidentally been switched. This could eliminate the possibility of inappropriate diagnosis or delivery of therapy.

The locator button could also be used to locate an associated pod. Although the pod is generally associated to the one base, events may occur in which there are multiple patients, and in turn, multiple bases and corresponding pods. During such events, the multiple pods may be inadvertently transposed, possibly due to identical equipment being used in regard to the multiple bases and pods. As discussed above, base 130 and pod 132 could provide circuitry or programming to sense the presence of another pod within its range at state 300 (or a specified distance for example five feet) and instruct the operator to manually press a button on the module at state 304. Pod 132, to which base 130 is associated, could respond, thereby eliminating confusion and possibly avoiding inappropriate diagnosis or delivery of therapy.

Figure 13:
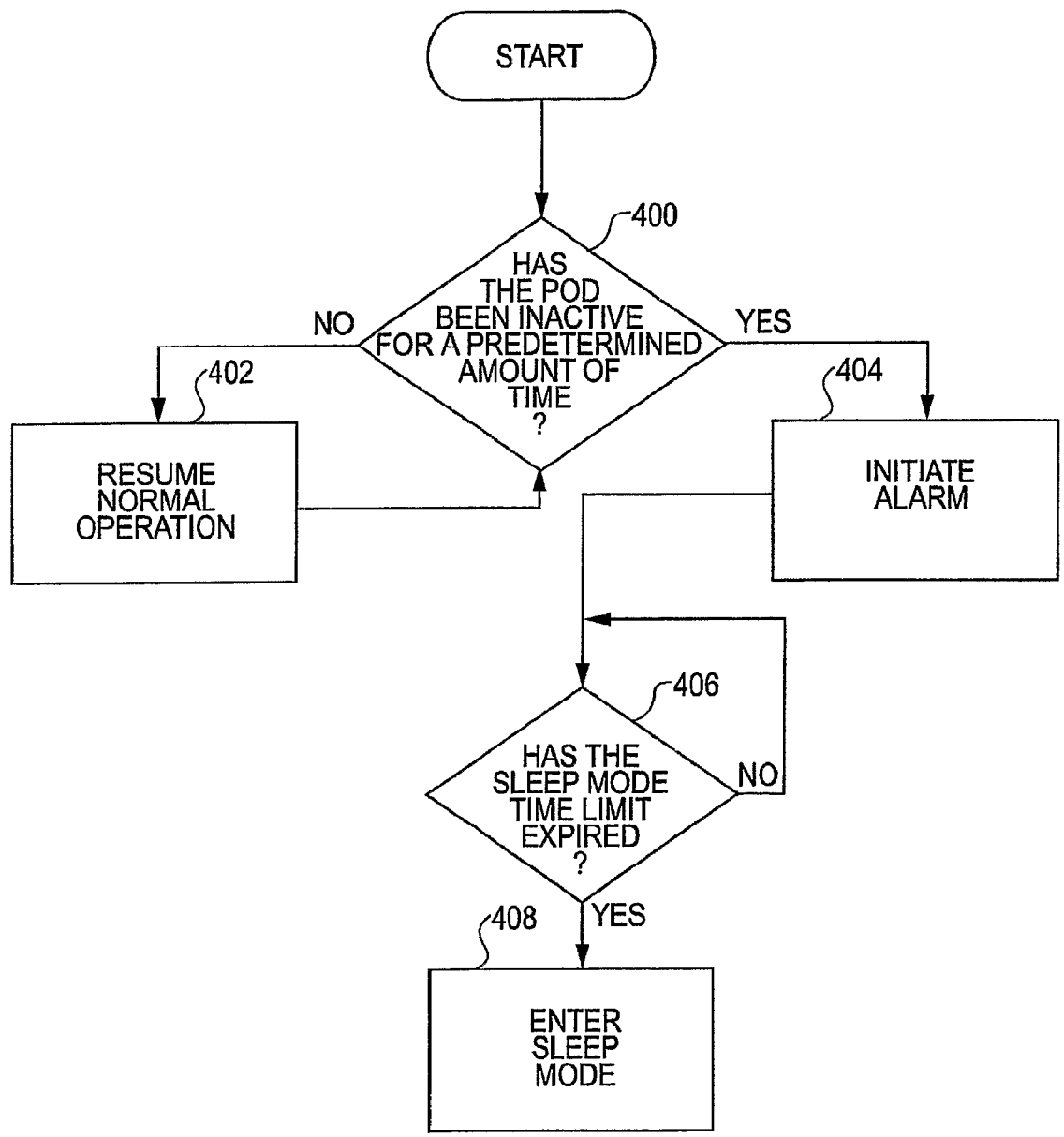
FIG. 13 is a flow diagram of a patient monitoring pod location function in an embodiment of the present teachings.

With reference to FIG. 13, a flow diagram of a pod location function in an embodiment of the present teachings is shown. It is contemplated that after having been taken off the base, the pod may be forgotten or lost. At state 400, if base 130 and pod 132 are not physically connected, base 130 periodically determines how long it has been since it had wireless communications with pod 132. If the amount of wireless inactivity is below a predetermined amount of time, then base 130 resumes normal operation at state 402. However, after a certain amount of wireless inactivity time between pod 132 and base 130, an alarm could go off at base 130 and/or pod 132 at state 404. If base 130 is turned off and pod 132 is remotely located, after a certain amount of inactivity time, such as several minutes (state 406), pod 132 could enter "sleep mode" (i.e., pod is on, but using a reduced amount of power to maintain its activation) to preserve power at state 408. When base 130 was turned back on, wireless communications could be used to detect pod 132, awaken pod 132, and initiate an audible alarm on pod 132 to indicate where pod 132 is located. Alternatively, the operator could initiate the pod finder action on the screen at base 130.

In certain embodiments, base 130 could act as a hub, which could talk to multiple pods. An operator interface is placed on the display screen of base 130 and allows the operator to select which pod to listen to. The operator could test each pod by sending a signal to a particular pod to determine which pod they are trying to connect to. The operator could press a button and the pod could blink or enunciate to the operator in some manner that it is linked to the base. Provided the pod and base are associated, a signal could instead be initiated by the pod to confirm that the pod is, in fact, talking to the base.

Configuring the base 130 as a hub could be especially helpful in situations where there was a large response team to several patients. Base 130 could allow the operator to select which pod they want to receive patient information from as noted above. Furthermore, base 130 could be able to make an automatic selection on which pod to show on the screen based upon a patient parameter that indicated the patient was in some sort of immediate danger. This could be performed by the system controller 94 routing all data into similar patient analysis algorithms, which could look for abnormalities in the signals. Under this hub configuration, base 130 could collect information from the multiple pods but could only display information from the one selected pod.

It may be helpful to monitor the wireless connection quality between the base and the pod over their lifetimes. Monitoring this connection could be helpful because each parameter measured by the pod 132 requires a certain amount of bandwidth to be wirelessly transmitted back to the base 130. If the signal quality from the pod 132 degrades to a certain level due to connection quality, then a warning could be issued to the operator indicating they may need to somehow direct connect the pod 132 to the base 130 either via a cable or dock pod 132 within base 130. Furthermore, the operator can have the bandwidth scheme automatically step down by requesting fewer parameters from the pod 132. Alternatively, the base and pod could automatically cease or postpone communication of non-critical information when the communications link degrades. For instance, the system controller 66 within pod 132 and the system control module 94 (including the Interconnect module 92) within base 130 could detect when the signal quality degrades (e.g., certain number of errors detected) to a threshold level and could step down communications to a level that merely includes patient vital signs.

One skilled in the art will appreciate that the present teachings can be practiced with embodiments other than those disclosed. The disclosed embodiments are presented for purposes of illustration and not limitation, and the present teachings are limited only by the claims that follow.

The invention claimed is:

1. A modular external defibrillator system for treating a patient, comprising:
 a base containing a display and an external defibrillator module configured to deliver a defibrillation shock to the patient;
 a first pod operable when separated from the base, the first pod having a first patient parameter module and connectable to the patient to collect first patient data related to at least a first patient vital sign, the first pod capable of wirelessly transmitting the first patient data to the base; and
 a second pod operable when separated from the base, the second pod having a second patient parameter module and connectable to the patient to collect second patient data related to at least a second patient vital sign independent from the first vital sign, the second pod capable of wirelessly transmitting the second patient data to the base,
 in which, when one of the first or the second patient data is transmitted to the base, the base is configured to display an aspect of the transmitted one of the first or the second patient data and in which while the base is receiving the first patient data, the base is configured to sense a nearby presence of the second pod, and provide an alert in response to sensing the second pod.

2. The external defibrillator system of claim 1, in which the external defibrillator module is configured to deliver the defibrillation shock based on the one of the first or the second patient data transmitted to the base.

3. The external defibrillator system of claim 1, in which the first pod contains an interpretive algorithm to analyze a patient condition based on the first patient data.

4. The external defibrillator system of claim 1, in which the one of the first or the second patient data that is transmitted to the base is encrypted.

5. The external defibrillator system of claim 1, wherein the external defibrillator system is configured to select one of the first or the second pods over the other to transmit to the base the patient data the selected pod collects, and wherein selection of the selected pod is based on which of the first or the second pods is electrically directly connected to the base.

6. The external defibrillator system of claim 5, in which a unique pod identifier is transmitted from the selected pod to the base.

7. A modular external defibrillator system for treating a patient, comprising:
 a base containing a display and an external defibrillator module configured to deliver a defibrillation shock to the patient;
 a first pod operable when separated from the base, the first pod having a first patient parameter module and connectable to the patient to collect first patient data related to at least a first patient vital sign, the first pod capable of wirelessly transmitting the first patient data to the base; and
 a second pod operable when separated from the base, the second pod having a second patient parameter module and connectable to the patient to collect second patient data related to at least a second patient vital sign independent from the first vital sign, the second pod capable of wirelessly transmitting the second patient data to the base,
 in which, when one of the first or the second patient data is transmitted to the base, the base is configured to display an aspect of the transmitted one of the first or the second patient data, and
 in which the base is configured to control which of the first or the second pods is selected over the other.

8. The external defibrillator system of claim 1, in which, when the base and the selected pod are communicating wirelessly over a link, if the link degrades, one of the base or the selected pod is configured to provide an alert.

9. The external defibrillator system of claim 1, in which, when the base and the selected pod are communicating wirelessly over a link, if the link degrades, less patient data is carried to the base.

10. The external defibrillator system of claim 1, in which, when the base and the selected pod are communicating wirelessly over a link, if the link is lost, the system is configured to output an alarm.

11. The external defibrillator system of claim 10, in which if the link is not reestablished within a preset time period after the alarm is output, the selected pod configured to enter a sleep mode.

12. The external defibrillator system of claim 7, in which a unique pod identifier is transmitted from the selected pod to the base.

13. The external defibrillator system of claim 7, in which the external defibrillator module is configured to deliver the defibrillation shock based on the one of the first or the second patient data transmitted to the base.

14. The external defibrillator system of claim 7, in which the first pod contains an interpretive algorithm to analyze a patient condition based on the first patient data.

15. A modular external defibrillator system for treating a patient, comprising:
 a base containing a display and an external defibrillator module configured to deliver a defibrillation shock to the patient;
 a first pod operable when separated from the base, the first pod having a first patient parameter module and connectable to the patient to collect first patient data related to at least a first patient vital sign, the first pod capable of wirelessly transmitting the first patient data to the base; and a second pod operable when separated from the base, the second pod having a second patient parameter module and connectable to the patient to collect second patient data related to at least a second patient vital sign independent from the first vital sign, the second pod capable of wirelessly transmitting the second patient data to the base, in which, when one of the first or the second patient data is transmitted to the base, the base is configured to display an aspect of the transmitted one of the first or the second patient data, and in which the selected pod is configured to provide an indication when prompted by the base to confirm that the selected pod has been selected over the other pod.

16. The external defibrillator system of claim 15, in which the external defibrillator module is configured to deliver the defibrillation shock based on the one of the first or the second patient data transmitted to the base.

17. The external defibrillator system of claim 15, in which the first pod contains an interpretive algorithm to analyze a patient condition based on the first patient data.

18. A method for a modular external defibrillator system for treating a patient, the system including: a base containing a display and an external defibrillator module configured to deliver a defibrillation shock to the patient, a first pod operable when separated from the base, the first pod having a first patient parameter module and connectable to the patient to collect first patient data related to at least a first patient vital sign, the first pod capable of wirelessly transmitting the first patient data to the base, and a second pod operable when separated from the base, the second pod having a patient parameter module and connectable to the patient to collect second patient data related to at least a second patient vital sign independent from the first vital sign, the second pod capable of wirelessly transmitting the second patient data to the base, the method comprising:

selecting one of the first or the second pods over the other;
establishing a communications link between the base and the selected pod, in which the one of the first or the second patient data collected by the selected pods is transmitted wirelessly to the base, while the base has the communications link established with the selected pod, sensing a nearby presence of the second pod, and providing an alert in response to sensing the second pod; and
displaying at the display an aspect of the transmitted one of the first or the second patient data.

19. The method of claim 18, further comprising:
delivering a defibrillation shock based on the one of the first or the second patient data transmitted to the base.

20. The method of claim 18, further comprising:
analyzing a patient condition based on an interpretive algorithm in the selected pod and the patient data collected by the selected pod.

21. The method of claim 18, in which the one of the first or the second patient data that is transmitted to the base is encrypted.

22. The method of claim 18, in which the selection is made by electrically directly connecting the one of the first or the second pods to the base.

23. The method of claim 18, in which a unique pod identifier is carried from the selected pod to the base.

24. The method of claim 18, in which if the link degrades, one of the base and the selected pod provides an alert.

25. The method of claim 18, in which if the link degrades, less patient data is carried to the base.

26. The method of claim 18, in which if the link is lost, an alarm is output.

27. The method of claim 26, in which if the link is not reestablished within a preset time period after the alarm is output, the selected pod enters a sleep mode.

28. A method for a modular external defibrillator system for treating a patient, the system including: a base containing a display and an external defibrillator module configured to deliver a defibrillation shock to the patient, a first pod operable when separated from the base, the first pod having a first patient parameter module and connectable to the patient to collect first patient data related to at least a first patient vital sign, the first pod capable of wirelessly transmitting the first patient data to the base, and a second pod operable when separated from the base, the second pod having a patient parameter module and connectable to the patient to collect second patient data related to at least a second patient vital sign independent from the first vital sign, the second pod capable of wirelessly transmitting the second patient data to the base, the method comprising:

selecting one of the first or the second pods over the other;
establishing a communications link between the base and the selected pod, in which the one of the first or the second patient data collected by the selected pods is transmitted wirelessly to the base, and in which the selected pod provides an indication when prompted by the base to confirm that the selected pod has been selected over the other pod; and
displaying at the display an aspect of the transmitted one of the first or the second patient data.

29. The method of claim 28, further comprising:
delivering a defibrillation shock based on the one of the first or the second patient data transmitted to the base.

30. The method of claim 28, further comprising:
analyzing a patient condition based on an interpretive algorithm in the selected pod and the patient data collected by the selected pod.

* * * * *

UNITED STATES PATENT AND TRADEMARK OFFICE
CERTIFICATE OF CORRECTION

| | | |
|---|---|---|
| PATENT NO. | : 8,738,128 B2 | Page 1 of 1 |
| APPLICATION NO. | : 13/103783 | |
| DATED | : May 27, 2014 | |
| INVENTOR(S) | : Christopher Pearce et al. | |

It is certified that error appears in the above-identified patent and that said Letters Patent is hereby corrected as shown below:

On the title page of the patent, first column, item 63:

Under the Section entitled "Related U.S. Application Data" replace "(63) Continuation of application No. 10/583,209, filed as application No. PCT/US2004/042377 on Oct. 18, 2007, now Pat. No. 7,957,798" with --(63) Continuation of application 10/583,209 filed Oct. 18, 2007, now Pat. No. 7,957,798, which is a 371 of PCT/US2004/042377, filed Dec. 17, 2004--.

On the title page of the patent, insert, item 30:

--(30) Foreign Application Priority Data

Apr. 22, 2004 (WO)   PCT/US2004/012421--.

Signed and Sealed this
Ninth Day of September, 2014

Michelle K. Lee
*Deputy Director of the United States Patent and Trademark Office*